United States Patent [19]

Spangle

[11] 4,408,489

[45] Oct. 11, 1983

[54] APPARATUS AND METHOD FOR MEASURING THE EXPANSION PROPERTIES OF A CEMENT COMPOSITION

[75] Inventor: Lloyd B. Spangle, Claremore, Okla.

[73] Assignee: The Dow Chemical Company, Midland, Mich.

[21] Appl. No.: 338,779

[22] Filed: Jan. 11, 1982

Related U.S. Application Data

[63] Continuation-in-part of Ser. No. 134,716, Mar. 27, 1980, abandoned.

[51] Int. Cl.$^3$ ...................... G01N 33/38; G01N 33/44
[52] U.S. Cl. ................................................. 73/432 R
[58] Field of Search ........................ 73/432 Z; 33/179

[56] References Cited

U.S. PATENT DOCUMENTS 3,779,085  12/1973  Rice .................................. 73/432 Z

*Primary Examiner*—Anthony V. Ciarlante
*Attorney, Agent, or Firm*—V. Dean Clausen

[57] ABSTRACT

An apparatus is disclosed which is useful for measuring the expansion properties of semi-solid materials which expand to a solid phase, upon curing, such as cement compositions. The apparatus includes a sleeve, preferably cylindrical, which has a vertical slit on one side, to allow the sleeve to expand. Mounted on the outside of the sleeve are several sets of pins, consisting of two pins each. The two pins in each set are located on opposite sides of the slit. In the test procedure, the sleeve is filled with wet cement, which is then cured to a solid. As the cement cures it causes the sleeve to expand. The actual expansion of the sleeve represents an expansion factor for the cement. This factor is calculated by measuring the distance across the pins of each set, when the sleeve is empty, and again after the cured cement expands the sleeve.

10 Claims, 2 Drawing Figures

APPARATUS AND METHOD FOR MEASURING THE EXPANSION PROPERTIES OF A CEMENT COMPOSITION

The Government of the United States of America has rights in this invention pursuant to Contract No. EG-77-C-02-4190 awarded by the U.S. Energy Research and Development Administration.

CROSS-REFERENCE TO RELATED APPLICATION

This application is a continuation-in-part of U.S. application Ser. No. 134,716, filed Mar. 27, 1980, and now abandoned.

BACKGROUND OF THE INVENTION

The invention relates broadly to an apparatus and method for measuring the expansion properties of cement compositions which are capable expanding during a curing or setting period. In a specific application, the apparatus is used to measure the expansion properties of a cement slurry composition, such as the type of material used in cementing of oil or gas wells.

In a typical well cementing operation, a cement slurry is run into the annulus between the well casing and the bore hole, frequently at more than one location in the bore hole. As the cement slurry hardens to a solid during the setting-up period, it is essential that the cement composition expand sufficiently to provide a good bond with the well casing and also the wall of the bore hole. Otherwise, if the cement should shrink during hardening, it can leave channels between the bore hole wall and the cement column and between the cement column and the well casing. This "channeling" effect is undesirable for several reasons. One reason is that gas or oil from a producing formation could leak into these channels and thus by-pass the production tubing which carries it to the well head.

Because of the problems mentioned above, it would be desirable to have a reliable procedure for measuring the expansion properties of cement compositions. The prior tests for determining expansion of cement compositions have not been entirely satisfactory. For example, one of the procedures in common use is a test derived by the American Society for the Testing of Materials, in which the cement slurry is put into a bar-type mold and cured underwater and at atmospheric pressure. During the curing cycle, the first time the cement bar is removed from the mold is when it is hard enough so that it won't break up as it comes out of the mold. After the bar is removed from the mold, it is carefully measured for length and then returned to the water curing bath to allow it to finish curing. Periodically, during the curing period, the bar is removed from the water bath and the length is measured each time.

The ASTM test has a major drawback. For example, when the bar is first removed from the mold, it is assumed that the cement has not cured long enough for the material to begin to expand. However, in reality, this point in time does not exist. Present studies clearly indicate that a cement composition will begin to expand from the moment it starts to set-up. In the prior procedure, therefore, it is virtually impossible to obtain reliable data on the expansion properties of cement compositions.

SUMMARY OF THE INVENTION

In the broad application of this invention, it provides an apparatus and method for measuring the expansion properties of a cement composition, which is capable of being cured to a solid phase, and which is expandable during the curing period. The basic apparatus comprises a sleeve which has a vertical slit therein. Mounted on the outside of the sleeve is at least one set of pins, which consists of two pins. As mounted on the sleeve, the two pins are in horizontal alignment with each other and they are located on opposite sides of the slit.

A single spring, such as a coil spring, is secured across the two pins. When the sleeve is empty, that is, before it is filled with an expandable cement composition, it is in a closed position. In the closed position, the sleeve is adapted for receiving and containing the cement composition prior to the curing step. As the material expands during curing, it causes the sleeve to open up or expand outwardly, such that the sleeve provides a container for holding the expanding cement. This apparatus also includes a means for measuring the distance between the pins. This measurement is taken when the sleeve is in its closed position, and again when it is expanded to the open position.

DESCRIPTION OF A PREFERRED EMBODIMENT

Figure 2:
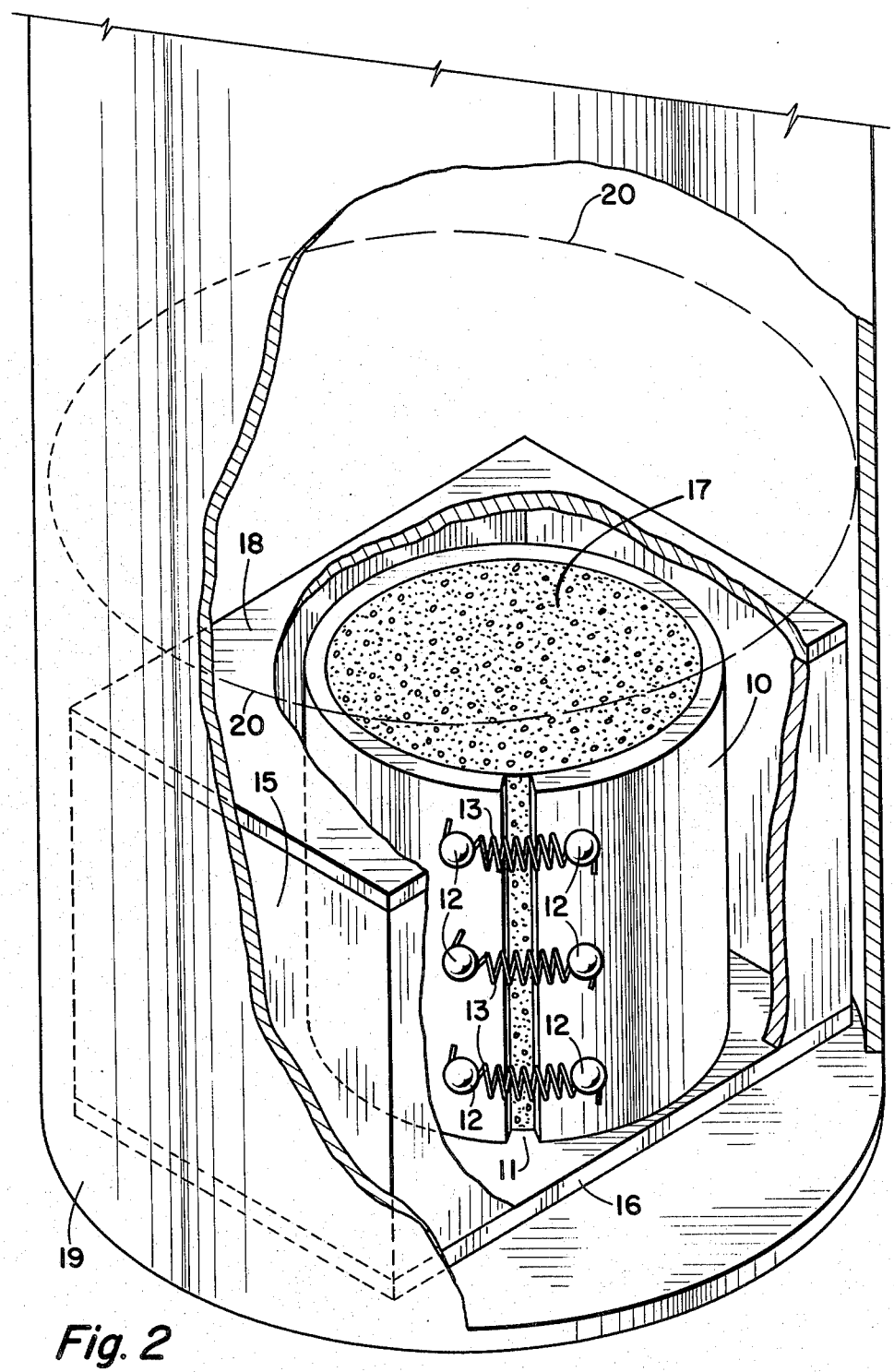
FIG. 2 is a perspective cut-away view, showing the sleeve component sitting inside of a retainer vessel. In this view the sleeve is filled with an expandable cement composition and it is in an open position.

In the drawing, the numeral 10 refers to a sleeve component of the present invention. As best shown in FIG. 2, there is a vertical cut along one side of the sleeve 10, which defines a vertical slit 11. Numeral 12 refers to a set of two round head pins, the pins being mounted on the outer wall surface of the sleeve and in horizontal alignment with each other. According to this invention, there is at least one set of pins mounted on the sleeve, with one of the pins being located on the left side of the slit 11 and the other on the opposite, or right, side of the slit. In a preferred embodiment, as illustrated in FIG. 2, there are three sets of pins 12 mounted on the sleeve 10.

Figure 1:
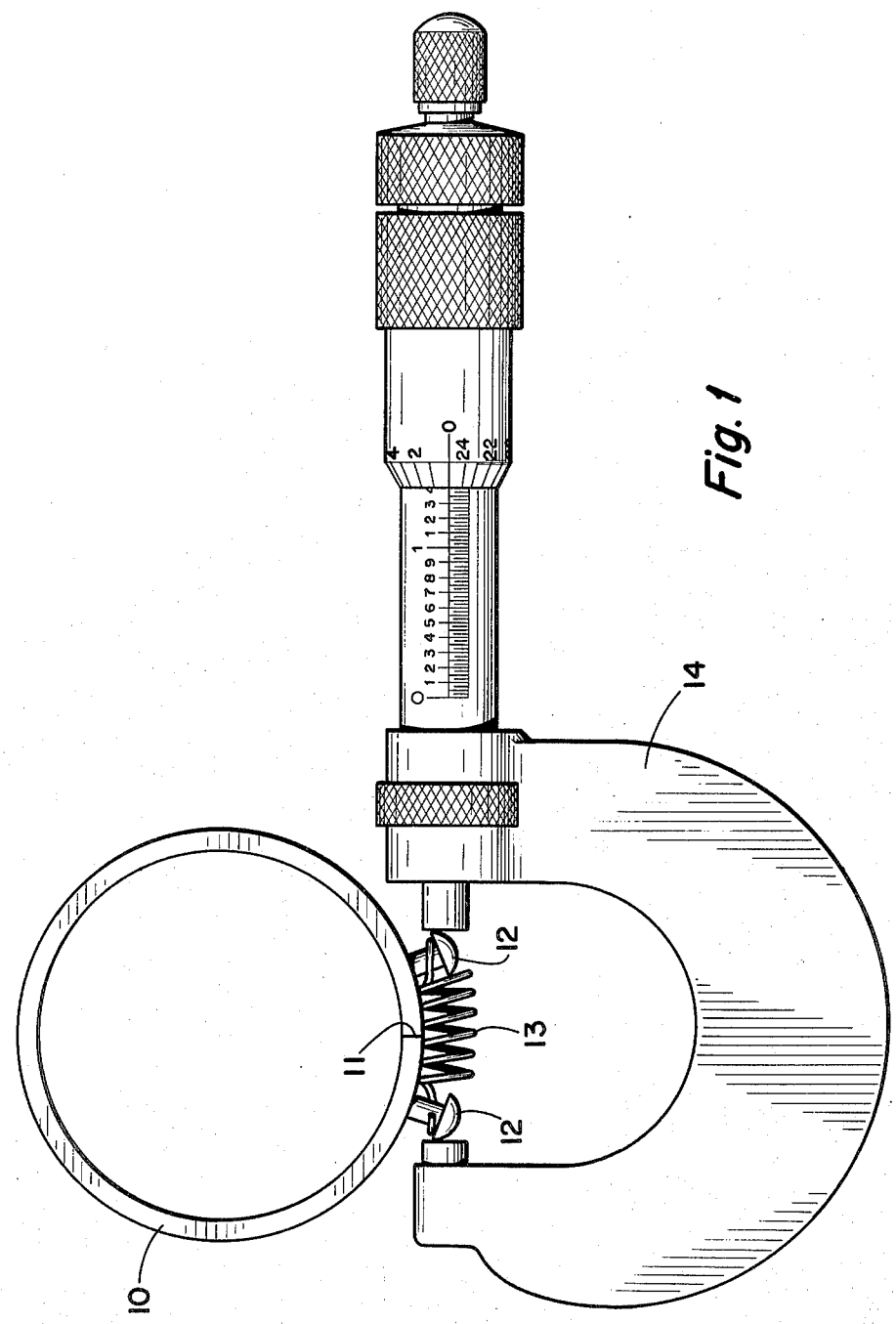
FIG. 1 is a plan view of a sleeve component of this invention, which includes pins mounted on the outside of the sleeve. In this view, the sleeve is in a closed position and a micrometer is illustrated as a means for measuring the distance between the pins on the sleeve.

A single spring 13, preferably a coil spring, is fastened across each set of the pins 12. Before the sleeve 10 is filled with an expandable material, as shown in FIG. 1, the spring 13 holds the opposing edges of the slit 11 in face-to-face contact with each other, such that the sleeve assumes a closed position.

OPERATION

The invention can be illustrated by describing a typical operation in which the apparatus described herein is used to measure the expansion properties of a hydraulic cement composition. The first step is to measure the linear distance between the pins 12 and each of the sets mounted on the sleeve 10. The measurement of each set of pins is taken with a conventional outside micrometer 14, when the sleeve is in its closed position, that is, prior to filling the sleeve with cement.

While the illustrated embodiment employs a manually operated measuring device, automated linear measuring devices, such as strain gauges or piezoelectric devices, could suitably be employed for the purpose. The sleeve is also held at a constant temperature and pressure while each set of pins is measured. According to this operation, the temperature is held constant at about 80° F. and the measurements are made at atmospheric pressure.

It is preferred that the sleeve 10 be of a cylindrical shape, as illustrated herein. However, sleeves of other shapes, such as rectangular, square, elliptical, and the like, could also be used in the practice of this invention. When other than a cylindrical sleeve is employed, it is preferable that more than one vertical slit be incorporated in the sleeve. This is to avoid the possibility that expansion of cement in a sleeve, with other than a circular horizontal cross section, would unduly distort the horizontal cross section. Such distortion could cause a single slit to open more than the actual linear expansion of the cement. However, since the linear expansion commonly encountered in most tests of hydraulic cements is about 1 percent or less, the error introduced by such distortion is usually insignificant and a single vertical slit will be sufficient in most cases.

After the pin measurements are taken, the sleeve 10 is placed inside of a suitable retainer vessel 15. One type of retainer vessel which may be used is a conventional cube mold, of the type used in testing cement compositions for compressive strength. Before placing the sleeve 10 in the vessel 15, the inner wall surface of the sleeve is coated with grease and a strip of tape is placed along the inside of the seam formed by the slit 11. The tape used for this purpose should have a high moisture and heat resistance, such as a Teflon (brand) tape. In the vessel 15, the upper surface of the base plate 16 is also coated with grease. This is done to prevent water loss from the cement composition during the expansion test.

After the empty sleeve has been placed inside the vessel 15, it is filled with a slurry form of the cement composition to be tested, as indicated by numeral 17. The sleeve is filled with the cement slurry and the slurry is then puddled to remove entrained air. If the slurry is thin enough to segregate, it is allowed to hydrate to the point that it has adequate viscosity to prevent segregation before placing in the sleeve.

A cover plate 18 is then secured to the retainer vessel 15 to enclose the cement-filled sleeve 10. This entire unit (the sleeve and retainer vessel) is then placed in an autoclave 19. The autoclave is filled with a liquid medium to a height such that the liquid completely covers the vessel 15 and sleeve 10. The liquid 20 provides the fluid medium necessary for curing the cement composition, and it also keeps the cement from shrinking during the curing step. Typically, the preferred liquid medium is water.

At this point the operator estimates the "working" temperature and pressure conditions likely to be present at the downhole zone which is to be cemented off. Typically, the temperature may range from about 15° F. to about 600° F., and the pressure will vary between atmospheric pressure and about 20,000 psig.

The liquid in the autoclave is then heated, by the autoclave heaters, to the predetermined temperature. At the same time, the predetermined pressure level is applied hydraulically to the autoclave atmosphere according to a known procedure. The cement composition is then allowed to cure for a period of time which is considered to be sufficient for the cement to form a good bond with the well casing and the wall of the bore hole. Typically, the curing period will be about seven days, with the temperature and pressure being held constant throughout this period.

When the curing period is finished, the entire unit (the sleeve 10 and vessel 15) is removed from the autoclave. At this point, the cement composition 17 inside of sleeve 10 has solidified and expanded, such that it has caused the circumference of the sleeve to increase in size. The sleeve is then brought back to the starting temperature of 80° F., in an environment of atmospheric pressure, so that the sleeve is in the identical condition that it was when the first pin measurements were taken.

The next step is to again measure the linear distance between each of the three sets of pins 12 on the expanded sleeve, using the micrometer 14 in the same manner as described earlier. The expansion of the cement composition during the curing step is then calculated from the following equation:

$$100\left[\frac{r}{R}\left(\frac{C_2}{C_1} - 1\right)\right]$$

where
$C_1$ = distance between pins when sleeve is empty
$C_2$ = distance between pins when sleeve is expanded
$R$ = inside radius of sleeve
$r$ = R plus length of the pin.

In the practice of this invention, when the sleeve 10 expands, in response to the expanding cement, it causes the circumference of the sleeve to change, as mentioned earlier. The equation set out above simplifies the calculation of the change in size of the inside diameter of the sleeve 10, resulting in percent linear expansion. Some error is introduced by the foregoing equation, which is an approximation that assumes the expansion is small, for example, on the order of one percent. But in relative terms, the information derived from this device, and the measurements taken, provide useful data when comparing different cement compositions under constant conditions.

It is also an advantage to be able to measure the expansion of the sleeve 10 at several points. For example, one measurement is taken across the pins mounted near the top of the sleeve, a second measurement across the pins mounted near the bottom of the sleeve, and a third measurement across the pins mounted between the bottom and the top set of pins. This gives the operator three separate measurements, which can then be averaged to provide a value representing the average linear expansion of the sleeve (in percent).

In the embodiment described and illustrated herein, only a single test unit is used. This single unit, as described earlier, is made up of only sleeve 10 and one retainer vessel 15 (cube mold). The reason for illustrating a single test unit herein is to simplify the drawing. In actual practice, more than one test unit may be used in a given operation. In an embodiment using more than one test unit, the retainer vessel can be a conventional mold unit which has two or more cube-shaped compartments positioned side-by-side. Also, the mold units are usually made to be stackable, one on top of the other.

The invention claimed is:

1. An apparatus for measuring the expansion properties of a cement slurry composition, which sets up to form a solid phase, and which is expandable during the setting-up period, the apparatus comprising:
   a sleeve having at least one vertical slit therein;
   the sleeve includes at least one set of pins, consisting of two pins, the pins are mounted in horizontal alignment on the sleeve, and the pins are located on opposite sides of the verical slit;
   at least one spring member, the spring member connects the two pins together;
   the sleeve has a closed position, in which it can receive and contain the cement slurry composition, and the sleeve has an open position, in which it expands outwardly, such that it can contain the cement composition as it expands during the setting-up period;
   a retainer vessel in which the sleeve is placed during the setting-up period of the cement slurry composition, and the retainer vessel completely encloses the sleeve and cement slurry composition during said setting-up period; and
   a pressure vessel which contains a liquid medium, and the retainer vessel, sleeve and cement slurry composition are placed in the pressure vessel, such that they are submerged in said liquid medium during the setting-up period of the cement slurry composition.

2. The apparatus of claim 1 which further includes a means for measuring the distance between the two pins in the set, when the sleeve is in its closed position, and when the sleeve is in its open position.

3. The apparatus of claim 2 in which the measuring means is a micrometer.

4. The apparatus of claim 1 in which the sleeve has a cylindrical shape.

5. The apparatus of claim 1 in which the sleeve has at least three sets of pins, including a first set of pins mounted near the top edge of the sleeve, a second set of pins mounted near the bottom edge of the sleeve, and a third set of pins mounted between the first and second set of pins.

6. The apparatus of claim 5 which includes a means for measuring the distance between the two pins in each of the recited pin sets.

7. The apparatus of claim 1 in which the liquid medium in the pressure vessel is water.

8. Method for measuring the expansion properties of a cement slurry composition capable of expanding during its setting-up period, comprising the steps of:
   placing an empty sleeve on a flat surface, the sleeve having at least one vertical slit therein, the sleeve including at least one set of pins, consisting of two pins, which are mounted on opposite sides of the vertical slit;
   measuring the distance between the pins in the set, when the sleeve is in a closed position, with the sleeve being held at a temperature of about 80° F., and in an environment of atmospheric pressure;
   filling the sleeve with a cement composition in a slurry form;
   placing the sleeve containing the cement slurry composition into a retainer vessel, which completely encloses the sleeve and cement slurry composition;
   placing the retainer vessel, and the sleeve containing the cement slurry composition, into a pressure vessel, and submerging these components in a liquid medium contained in the pressure vessel;
   inducing a predetermined pressure, above atmospheric pressure, within the pressure vessel;
   heating the liquid medium in the pressure vessel to a temperature sufficient to cause the cement slurry composition to set-up to a solid phase at the said predetermined pressure, the said temperature being above 80° F.;
   causing the sleeve to move outwardly to an open position, as the cement slurry composition expands during its setting-up period;
   removing the sleeve containing the solid phase cement from the retainer vessel and the pressure vessel;
   placing the sleeve in an environment of atmospheric pressure, and reducing the temperature to about 80° F.; and
   again measuring the distance between the pins in the set, while the sleeve is in its open position.

9. The method of claim 8 in which the pressure induced into the pressure vessel is between about atmospheric pressure and 20,000 psig.

10. The method of claim 8 in which the liquid medium in the pressure vessel is heated to a temperature of between about 15° F. and 600° F.

* * * * *